United States Patent
Fucci et al.

[19]

[11] Patent Number: 5,827,291
[45] Date of Patent: Oct. 27, 1998

[54] SUTURE ANCHOR DRIVER WITH SUTURE RETAINER

[75] Inventors: Joseph Fucci, Palm Harbor; A. Frank Trott, Largo, both of Fla.

[73] Assignee: Linvatec Corporation, Largo, Fla.

[21] Appl. No.: 744,178

[22] Filed: Nov. 5, 1996

[51] Int. Cl.[6] .................................................. A61B 17/00
[52] U.S. Cl. ...................... 606/104; 606/139; 606/232
[58] Field of Search ................................. 606/104, 148, 606/144, 151, 139, 232, 73, 75

[56] References Cited

U.S. PATENT DOCUMENTS

| | | |
|---|---|---|
| 4,632,100 | 12/1986 | Somers et al. . |
| 5,071,420 | 12/1991 | Paulos et al. ............................ 606/104 |
| 5,100,417 | 3/1992 | Cerier et al. . |
| 5,102,421 | 4/1992 | Anspach, Jr. . |
| 5,141,520 | 8/1992 | Goble . |
| 5,156,616 | 10/1992 | Meadows et al. . |
| 5,207,679 | 5/1993 | Li . |
| 5,217,486 | 6/1993 | Rice et al. . |
| 5,224,946 | 7/1993 | Hayhurst . |
| 5,258,016 | 11/1993 | Dipoto et al. . |
| 5,261,914 | 11/1993 | Warren . |
| 5,324,308 | 6/1994 | Pierce . |
| 5,354,298 | 10/1994 | Lee et al. . |
| 5,411,506 | 5/1995 | Goble et al. . |
| 5,411,523 | 5/1995 | Goble . |
| 5,522,845 | 6/1996 | Wenstrom, Jr. . |
| 5,545,178 | 8/1996 | Kensey et al. . |
| 5,584,860 | 12/1996 | Goble et al. ............................ 606/104 |

*Primary Examiner*—Jeffrey A. Schmidt
*Attorney, Agent, or Firm*—Gene Warzecha

[57] ABSTRACT

An elongated suture anchor driver having a suture retaining means at its proximal end. The driver receives a suture anchor at its distal tip and has a throughbore for enabling suture attached to the suture anchor to pass through the driver from its distal end to its proximal end. The proximal end of the driver is provided with a channel and a fixed post for guiding the suture exiting from the throughbore into an annular recess. A spring loaded slidable cylindrical sleeve acts against the suture in the recess to frictionally retain the suture, thereby securing the suture anchor and suture within the driver.

13 Claims, 9 Drawing Sheets

SUTURE ANCHOR DRIVER WITH SUTURE RETAINER

BACKGROUND OF THE INVENTION

1. Field of the Invention

The invention relates to a surgical instrument for inserting a surgical implant such as a suture anchor having an implantable body designed for insertion into tissue at a surgical site, the body having suture attached for securing selected tissue adjacent to the site. More particularly, the invention relates to an endoscopic surgical instrument for endoscopically driving a suture anchor having suture attached thereto.

2. Description of the Prior Art

In the course of certain surgical procedures, soft tissue is secured to a selected bone surface either directly, via some type of implant, or indirectly via an implant (i.e. an anchor) to which suture is attached, the suture then being tied to the soft tissue to hold it in place. Anchors may be used to attach soft tissue such as ligaments, tendons, muscles, etc. to a surface from which the soft tissue has become detached and may also be used to secure soft tissue to supplementary attachment sites for reinforcement. For example, in urological applications anchors may be used in bladder neck suspensions to attach a portion of the bladder to an adjacent bone surface. Such soft tissue attachment may be done during either open or closed surgical procedures, the latter being generally referred to as arthroscopic or endoscopic surgery. The terms "arthroscopic" and "endoscopic" may be used interchangeably herein and are intended to encompass arthroscopic, endoscopic, laparoscopic, hysteroscopic or any other similar surgical procedures performed with elongated instruments inserted through small natural or artificial openings in the body.

In procedures requiring suturing of soft tissue to bone, the suture is first anchored by the so-called suture anchors to the bone before suturing of the soft tissue. The prior art includes numerous types of suture anchors adapted to be secured in the bone, sometimes directly, in one step, and sometimes in pre-drilled holes or tunnels. The term "suture anchor" is used broadly and will be understood to refer to devices having a similar structure even if material other than suture is connected to the device. Some prior art suture anchors are elongated and have annular ribs or radially extending barbs and are required to be pushed or hammered directly into bone or into a pre-formed bone tunnel (exemplified by U.S. Pat. Nos. 5,102,421 (Anspach, Jr.); 5,141,520 (Goble et al.); 5,100,417 (Cerier et al.); 5,224,946 (Hayhurst et al.) and 5,261,914 (Warren)). Pushing an anchor into place has the disadvantage of potential trauma and damage to surrounding bone tissue, and has limited applicability where the location of the bone tunnel or pre-drilled hole is not axially aligned with (for example) an arthroscopic portal to permit transmission of the impacting force through an impactor to the anchor. An impacted suture anchor is not easily removable without damaging the bone into which it has been placed. Consequently, threaded suture anchors are often used as exemplified by U.S. Pat. Nos. 5,156,616 (Meadows et al.) and 4,632,100 (Somers et al.). Depending upon the type of threaded anchor, the insertion procedure may enable direct threading of the anchor into the bone or it may sometimes require that a pilot hole first be drilled into the bone, the hole then either enabling an anchor to be screwed in or enabling threads to be tapped to receive the anchor.

Both push-in and turn-in suture anchors have an implantable body with a distal end for being inserted into the bone and a proximal end serving as a drive portion. Each type of anchor has an eyelet somewhere along its length (or some other means) for attaching a suture to the body and is implanted by a driver adapted to engage the drive portion to either push it or turn it into a selected site. The anchor is usually driven with suture already threaded through the eyelet and the suture is then passed through tissue to be supported by the anchor, the suture ends then being tied or otherwise secured to the soft tissue. Suture anchors may be either pre-loaded with suture already attached or they may be provided to the user without suture. In the former case, the anchors may be packaged already assembled with a driver but in both cases, as stated above, the suture anchor is driven into the bone with the suture attached. Consequently, the driver must somehow accommodate the proximal ends of suture extending proximally from the anchor body as the latter is pushed or turned into the bone.

It is preferable to control the suture extending proximally from the suture anchor. In some instances the suture attached to push-in anchors simply follows the path of the driver in an uncontrolled manner such as shown, for example, in U.S. Pat. No. 5,207,679 (Li) and U.S. Pat. No. 5,217,486 (Rice et al.). It is known, however, to control the ends of the suture in other types of push-in suture anchor embodiments such as shown in U.S. Pat. No. 5,258,016 (DiPoto et al.). This patent shows the proximal ends of suture being wrapped around one or more retention posts attached to the proximal end of the driver. In one embodiment shown by DiPoto et al., the driver is cannulated throughout its length and the suture extends through the driver from its distal tip (to which the suture anchor is secured) to its proximal end where it is wrapped around a retention post. The tighter the suture is wound, the better it is held. Another push-in type driver is shown in U.S. Pat. No. 5,522,845 (Wenstrom Jr.) in which the proximal ends of the suture are wrapped around the proximal end of the driver in a recess between a toroidal grommet (O-ring) and the driver shaft. The grommet may stretch and break with use, especially with a large number of sterilization cycles, so such drivers are not optimized for repeated use. Additionally, the grommet design requires the user to aim the suture into the small tight space next to the grommet and is not easily adaptable to changes in suture size. All such drivers either require excessive manipulation of the proximal ends of the suture or do not securely hold the suture. Furthermore, such drivers have a frictional grip on the suture which is dependent on the suture diameter. A simpler and more secure suture retaining device would be preferable, especially for endoscopic applications. It would also be preferable to have a suture retaining device that operates independently of the suture size.

Drivers used for driving turn-in anchors must accommodate the proximal ends of the suture extending from the anchor since these ends would otherwise tend to get twisted and tangled and interfere with the procedure. The aforementioned Wenstrom Jr. patent shows one suitable driver and U.S. Pat. Nos. 5,411,506 (Goble et al.) and 5,411,523 (Goble) show another type of driver which secures the proximal ends of the suture to prevent tangling. These devices, however, are more suitable for manufacturing pre-loaded suture anchors and drivers as disposable assemblies which may then be used without further modification. That is, a user need simply remove the suture anchor/driver assembly from its package and place the suture anchor at the surgical site (manually or, preferably, with a powered drill). These devices are not reusable and impractical for use if the surgeon must thread the suture through the suture anchor prior to use or in a variety of other situations For example, a driver may occasionally need to be re-loaded if a suture anchor is incorrectly placed, if the anchor should become dislodged from the driver prematurely, etc.

It is accordingly an object of this invention to produce a suture anchor driver provided with a means for retaining suture attached to the anchor body.

It is still another object of this invention to produce a suture anchor driver for driving a suture anchor having suture attached thereto, the suture anchor driver being provided with a suture retaining means at its proximal end.

It is also an object of this invention to produce a suture anchor driver for driving a suture anchor having suture attached thereto, the suture anchor driver being reusable and capable of more securely holding suture than prior art devices.

It is another object of this invention to produce a suture anchor driver for driving a suture anchor having suture attached thereto, wherein the strength of the hold on the suture is independent of suture size.

SUMMARY OF THE INVENTION

These and other objects are accomplished by the preferred embodiment disclosed herein which is a driver for driving a suture anchor having suture attached thereto. The driver comprises an elongated shaft having a proximal end, a distal end and an anchor receiving means at the distal end of the shaft for receiving a suture anchor. A throughbore enables suture to pass from the distal end to the proximal end of the shaft and a suture retaining means at the proximal end of the shaft holds the suture securely. The holding means comprises a fixed retention means immovably secured to the shaft for guiding the suture in a predetermined direction, a movable compression means and a spring for urging the compression means toward the fixed retention means to retain the suture.

The invention also resides in a method for securing a suture anchor, with suture attached thereto, to a driver having a proximal end and a distal end comprising the steps of passing the suture from the distal end to the proximal end and providing at the proximal end a spring actuated suture retaining means for retaining suture. The retaining means comprises a fixed retention means immovably secured to the driver for guiding the suture in a predetermined direction, a movable compression means movably attached to the driver and a spring for urging the compression means toward the fixed retention means. The method further comprises retracting and holding the compression means, passing the suture between the fixed retention means and the compression means and then releasing the compression means to thereby secure the suture between it and the fixed retention means.

DESCRIPTION OF THE PREFERRED EMBODIMENT

Figure 1:
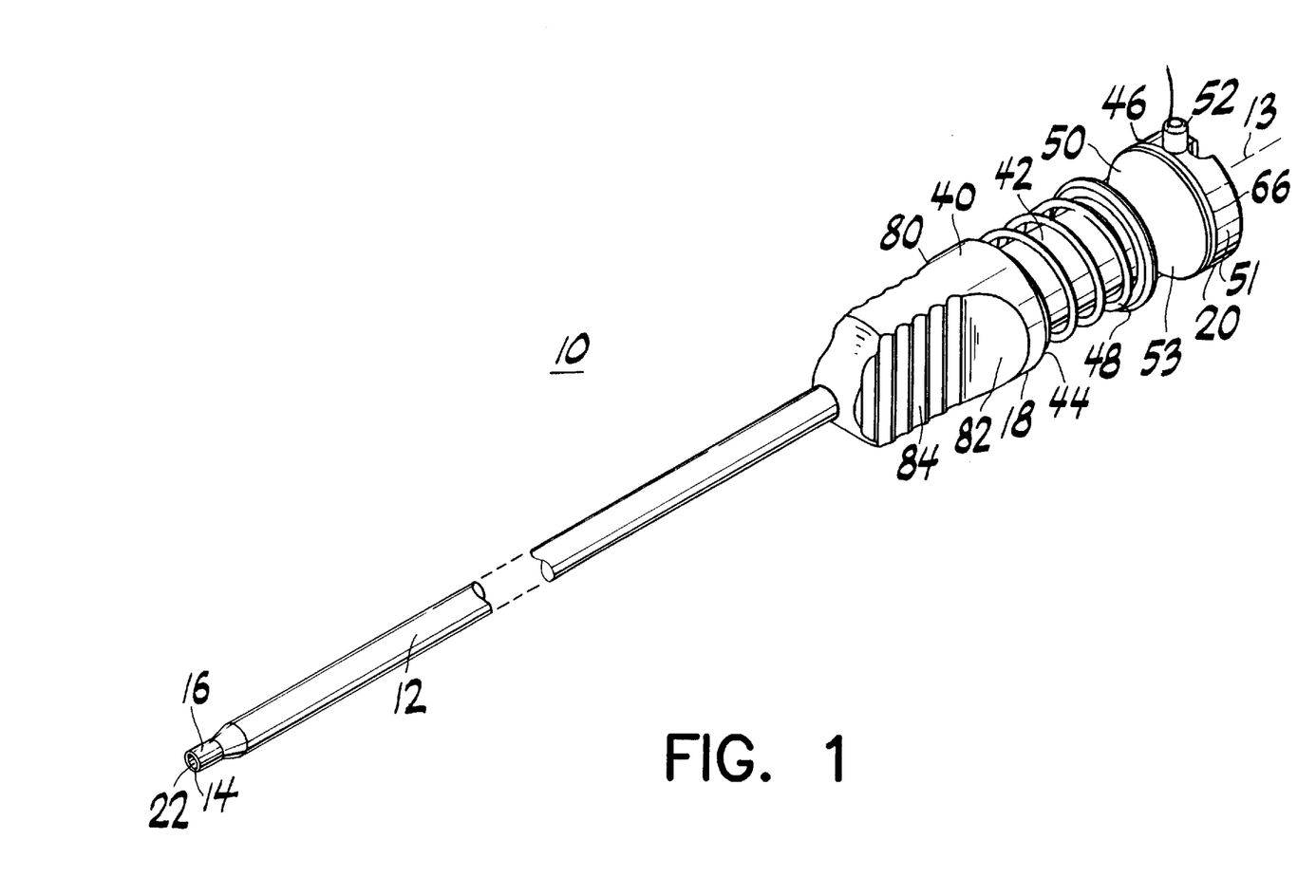
FIG. 1 is a front perspective view of a suture anchor driver constructed in accordance with the principles of this invention.
Figure 2:
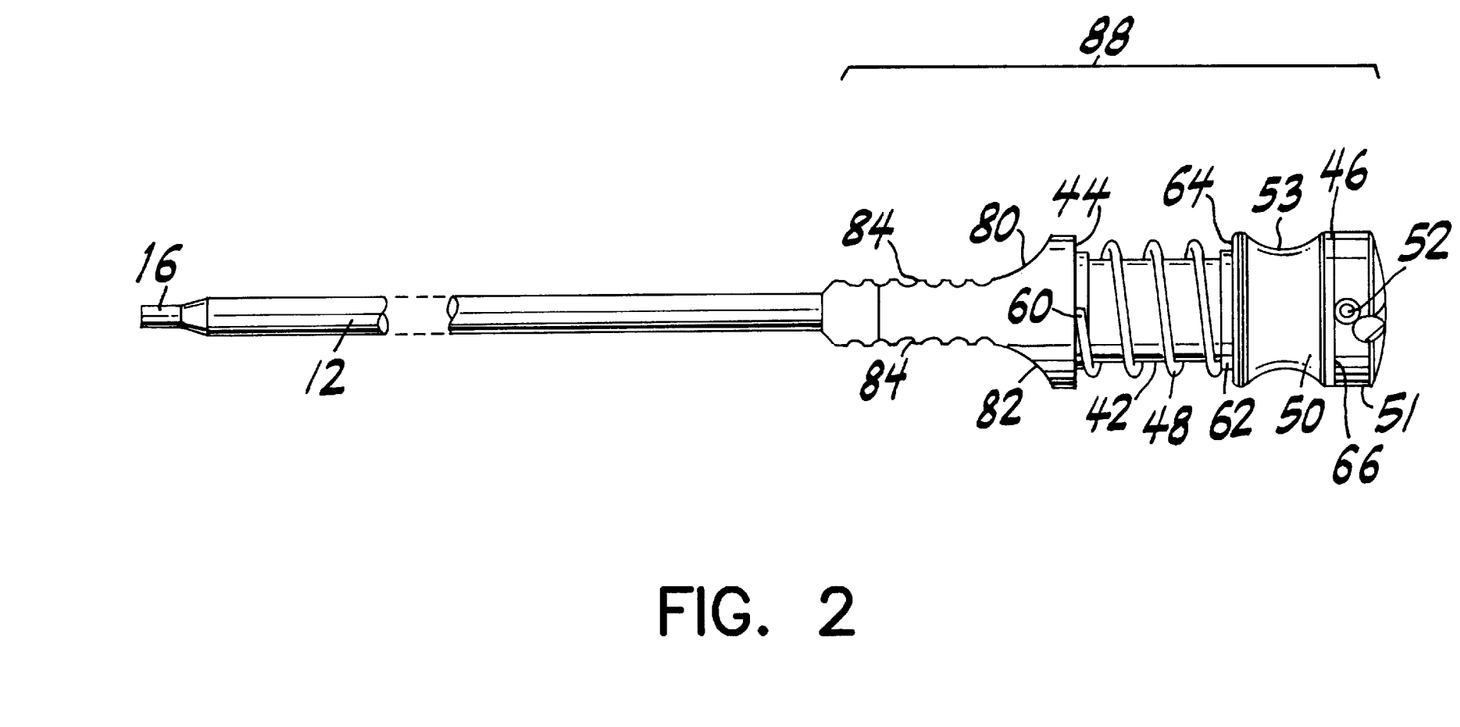
FIG. 2 is a top plan view of FIG. 1 showing the suture retaining means in a closed position, without suture.

As shown in FIGS. 1 and 2, driver 10 comprises a cannulated drive shaft 12 having an axis 13, an implant retaining portion 14 at its distal end 16 and a handle portion 18 at its proximal end 20. Throughbore 22 extends from distal end 16 to proximal end 20.

Figure 3:
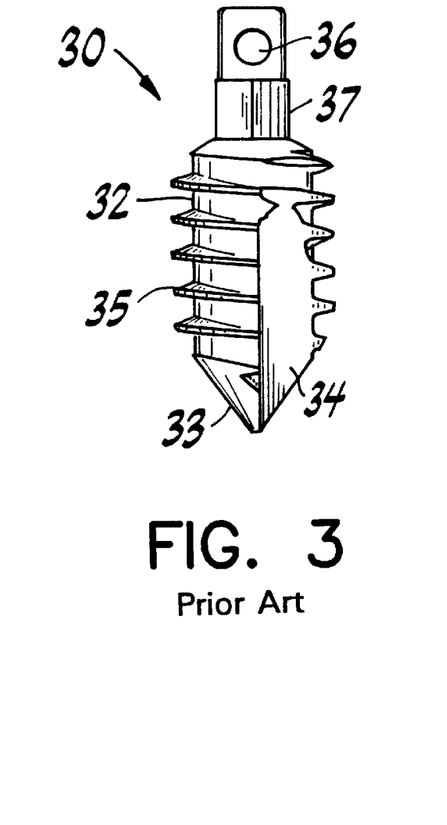
FIGS. 3 and 3A are side elevational views of prior art suture anchors.
Figure 3A:
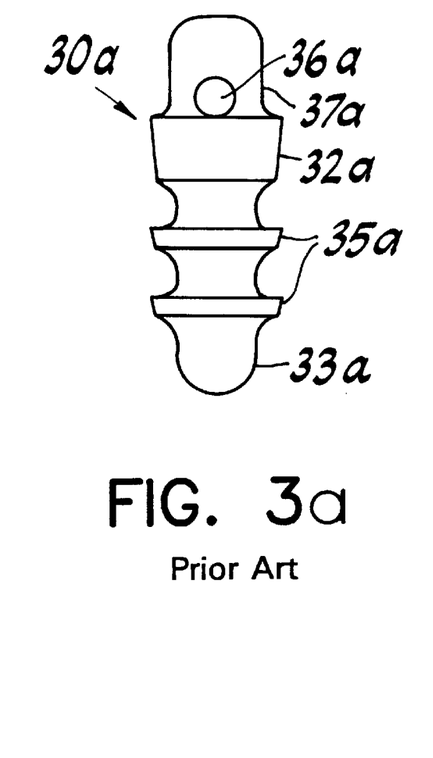
Figure 4:
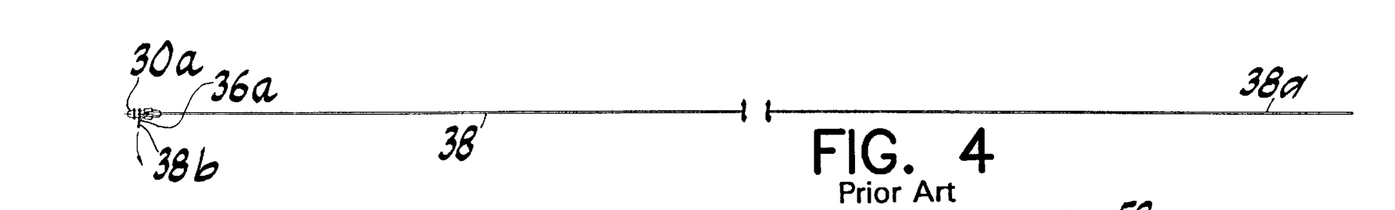
FIG. 4 is a side elevational view of a prior art suture anchor with a suture threaded through its proximal end.

Driver 10 is intended for use with either a turn-in or push-in implant such as anchor 30 (FIG. 3) or anchor 30a (FIG. 3A), respectively. These anchors are shown by way of example only and it will be understood that other anchors may be used with the invention. The component parts of each anchor are similar and will be numbered the same except that the push-in anchor parts will have the suffix "a". Suture anchors 30 and 30a each have an implantable body 32 and 32a, the former having a drill tip 33 and flute 34 at its distal end while the latter has a rounded tip 33a. The body of anchor 30 has a thread 35 while that of 30a has a plurality of annular ribs 35a. Each has an eyelet 36 and 36a or other means at its proximal end for engaging a length of suture 36 (best seen in FIG. 4). Anchors 30 and 30a have non-circular drive portions 37 and 37a which are adapted to be received in the distal implant retaining portion 14 of driver 10. As will be understood below, driver 10 captures and secures either implant to itself by means of tension translated to the implant via suture 38 that is passed through the eyelet of the implant. The distal end 16 is provided with a non-circular aperture (at 14) to receive the suture anchor drive portion 37 or 37a, as the case may be.

Handle portion 18 preferably has a larger diameter than shaft 12 to facilitate its manipulation and its outer surface 40 has an elongated annular recess 42 around its circumference that is bounded by distal and proximal shoulders 44 and 46, respectively. Recess 42 retains a coil spring 48 and a longitudinally slidable cylindrical sleeve 50. The diameter and shape of sleeve 50 may vary. For example, as shown in FIGS. 1 and 2 the diameter of the sleeve is equal to that of the adjacent proximal end 51 of the handle while in FIGS. 11 and 12 it is greater. An annular groove 53 enables a user to operate sleeve 50 from any annular position about the axis of driver 10. A fixed, radially outwardly extending post 52 is secured to the proximal end 51 of handle 18 and is used for guiding suture 36 into and around the recess 42 (best seen in FIGS. 8 and 9). While in the preferred embodiment post 52 is situated preferably immediately adjacent proximal shoulder 46 to guide suture directly into recess 42, it will be understood that other guiding structures may be suitable (for example, if the lead-in radial channel 77 described below is deep enough, a separate guide post may be unnecessary). The distal end 60 of spring 48 is longitudinally held in position by distal shoulder 44 at one end of recess 42 while the proximal end 62 of the spring lies against the distal end surface 64 of cylindrical sleeve 50. As will be understood below, the structure at the proximal end of driver 10 thus comprises a suture retainer because suture passing through the bore of the driver and connected to a suture anchor at the distal tip of the driver will be captured between the proximal surface 66 of sleeve 50 and proximal shoulder 46 of recess 42 due to the force of spring 48 against the distal end of the sleeve. The compression force of the spring against the sleeve causes a friction fit between the suture and sleeve which prevents the suture from sliding and thus prevents the anchor from disengaging from the distal tip of the driver. The spring also enables the retention mechanism to exert a force on the suture that is independent of suture size.

Figures 5, 6, 7:
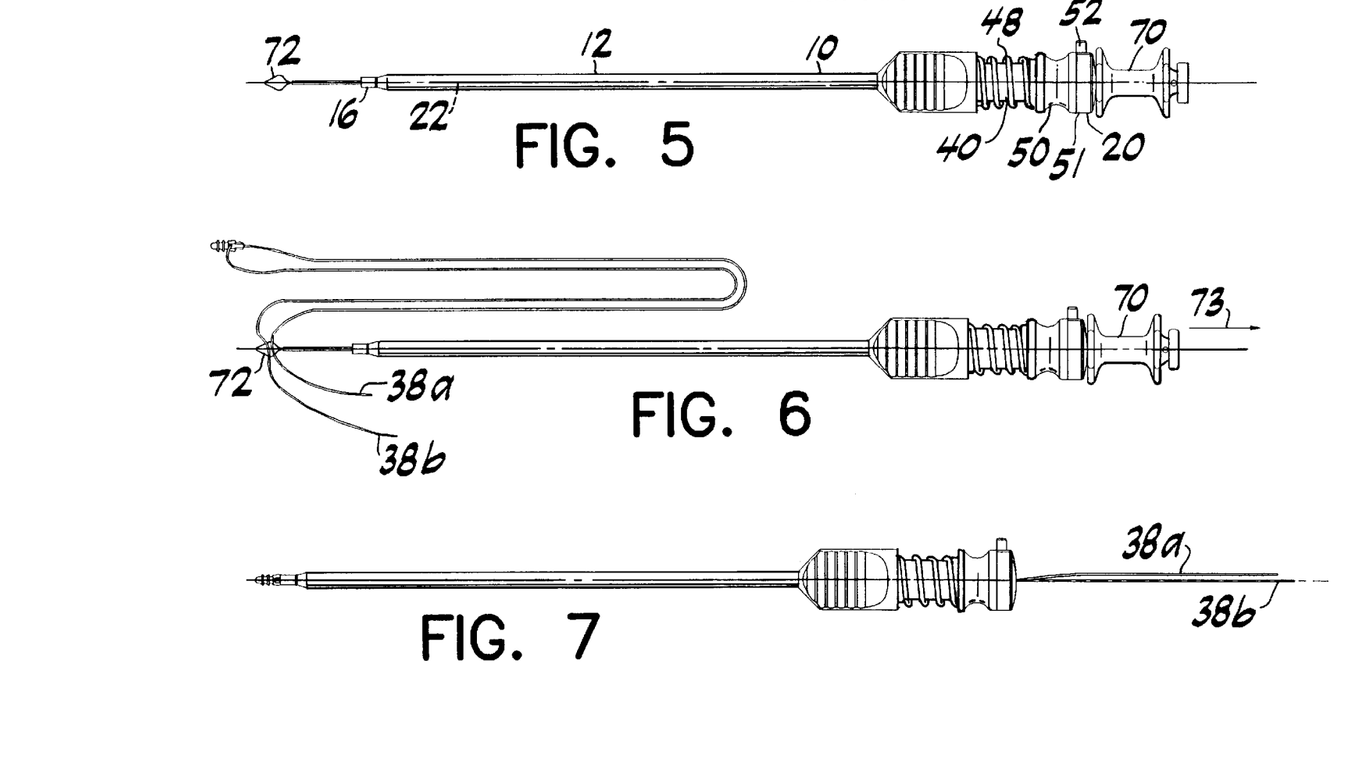
FIG. 5 is a side elevational view of the driver of FIG. 1 assembled with a suture threader.
FIG. 6 is a view of FIG. 5 showing the step of threading the suture of FIG. 4 through the suture threader of FIG. 5.
FIG. 7 is a view of another step of the method of using the invention in which the suture anchor is seated at the distal tip of the driver.
Figure 8:
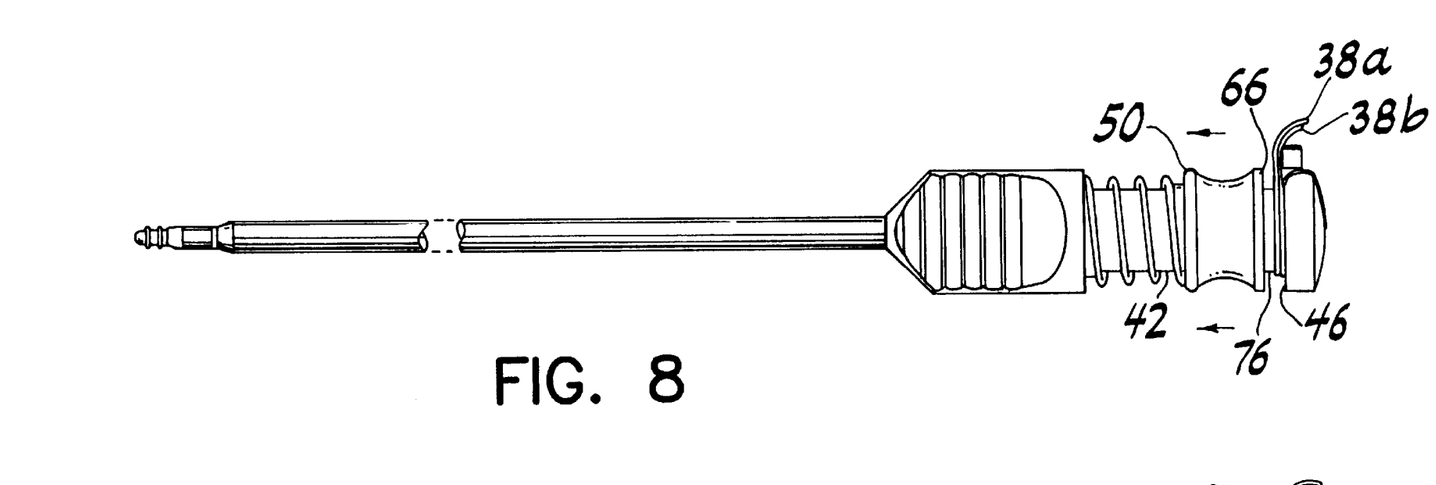
FIG. 8 is a view showing another step in the procedure in which the suture is wrapped around the proximal end of the driver.
Figure 9:
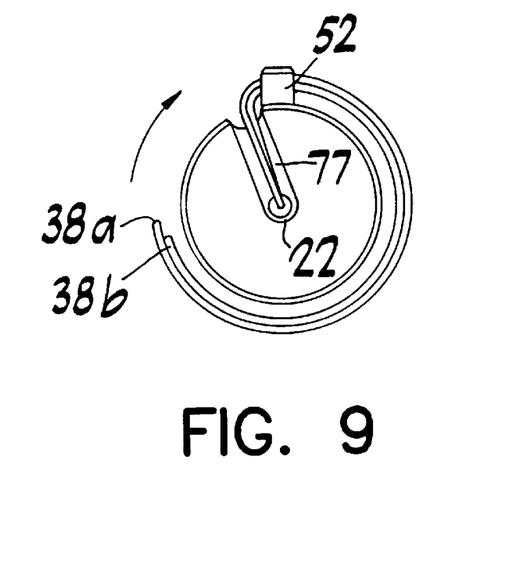
FIG. 9 is an end view of FIG. 8.
Figure 10:
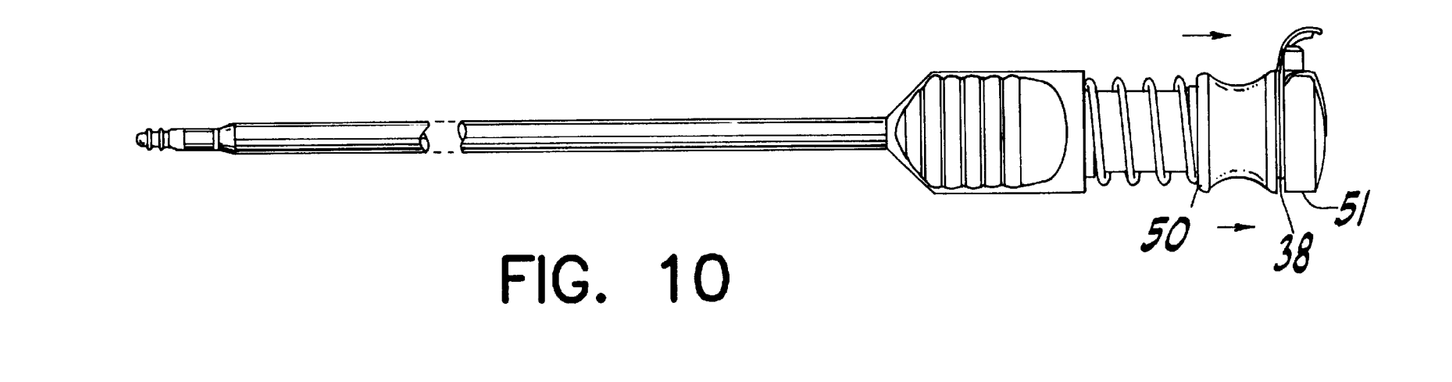
FIG. 10 is a view showing the next step in the procedure in which the driver frictionally engages the suture wrapped around its proximal end.

The method of using the driver is shown in FIGS. 4–10 with respect to suture anchor 30a. It will be understood that this method facilitates capturing distal parts of the suture ends in a suture retaining means at the proximal end of the driver. Suture 38 is threaded through eyelet 36a of the suture anchor 30a (FIG. 4) and the two ends 38a and 38b of the suture 38 are passed through bore 22 of the cannulated driver from the distal tip 16 and out the proximal end 20. The passage of the suture through the driver bore is accomplished easily with a conventional suture threader 70 (FIG. 5), the loop 72 of which receives the suture ends (FIG. 6) and is then pulled back out of the bore in the direction of arrow 73. The proximal end of the anchor is then seated in the distal tip 16 of the driver as shown in FIG. 7. Cylindrical sleeve 50 is slid distally (FIG. 8) to expose an annular proximal-most portion 76 of recess 42 while suture ends 38a, 38b coming out of the proximal end of bore 22 are guided into a radial channel 77, around post 52 (FIG. 9) in order to alter the suture direction and then around and into the distal end of recess 42 between proximal shoulder 46 and the proximal surface 66 of sleeve 50. Channel 77 enables the suture to lie below the proximal surface of end 51 so that the end may be struck or grasped without harming the suture. It will be understood that FIG. 9 shows the suture loosely wrapped about handle recess 42 for clarity; in use it is tighter, as shown in FIGS. 8 and 10. The retraction of the sleeve exposes a large area of the recess so suture of any size (within a range limited by the size of throughbore 22) can be easily wound around recess 42 without much attention by a user. The sleeve is then released (FIG. 10) allowing spring 48 to force it proximally, thus capturing suture 38 between the sleeve and the proximal shoulder of the recess. While in the preferred embodiment, the cylindrical shape of the sleeve (and annular groove 53) enables it to be activated from any direction around the driver axis, it will be understood that other shapes and structures will be suitable.

While the preferred embodiment utilizes a throughbore 22 to pass the suture from the distal end to the proximal end of the driver, it will be understood that a channel (not shown) on the outer surface of the driver (or some other means for communicating the suture to the proximal end) could be used.

Handle 18 may be provided with a pair of finger recesses 80 and 82 and friction enhancing ridges 84. The proximal end 51 of handle 18 may be threadably (or otherwise detachably) attached to a body portion (extending a length 88) to facilitate disassembly and cleaning by allowing the spring and sleeve to be removed.

Figure 11:
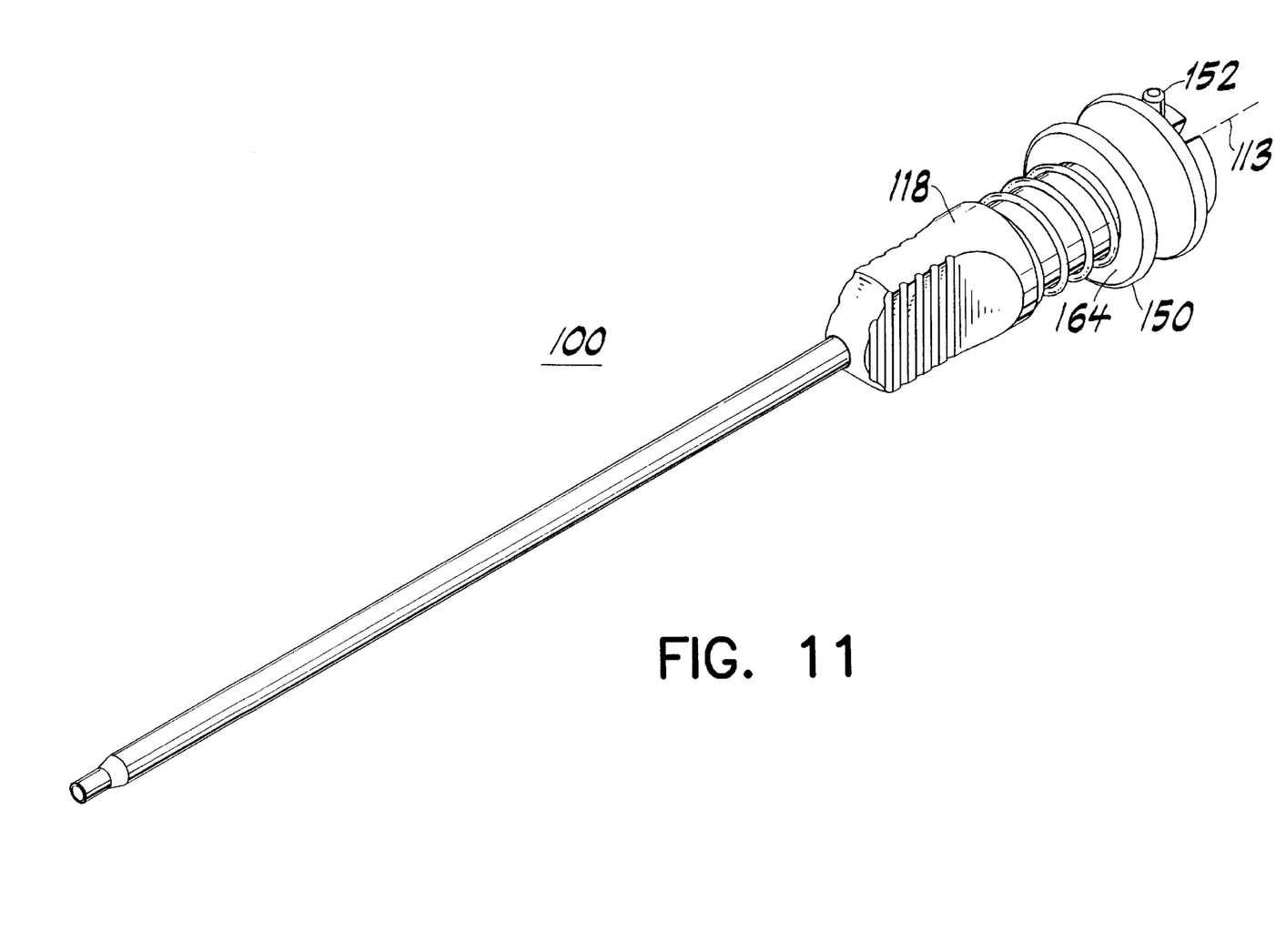
FIG. 11 is a front perspective view of an alternate embodiment of a suture anchor driver constructed in accordance with the principles of this invention.
Figure 12:
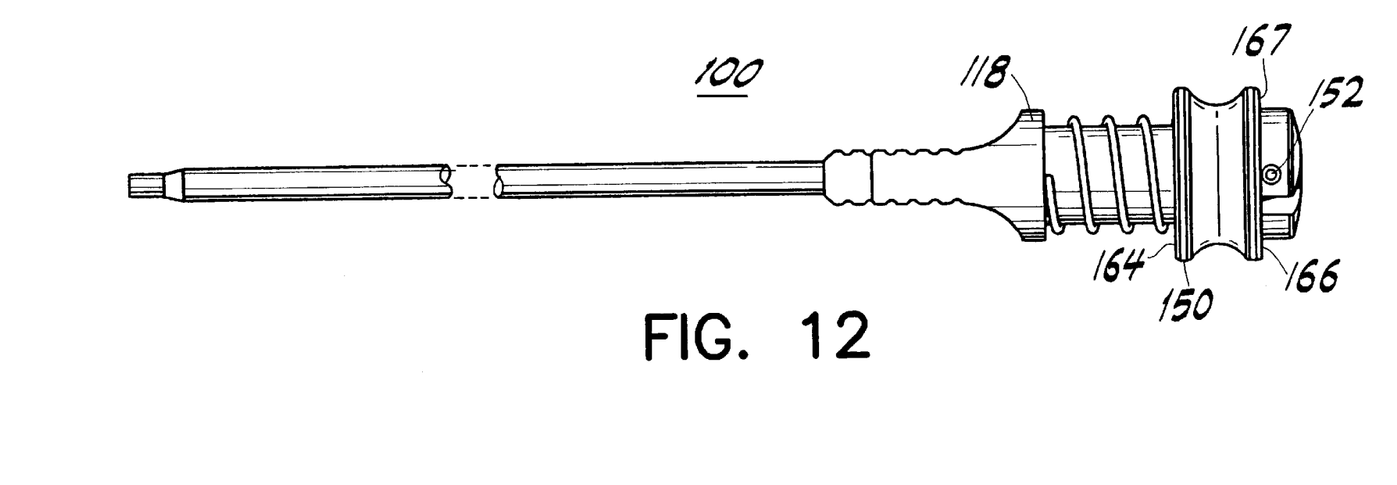
FIG. 12 is a top plan view of FIG. 11.

An alternate embodiment of the invention is shown in FIGS. 11 and 12 as suture anchor driver 100 which differs from driver 10 only in the configuration of handle portion 118. More particularly, this embodiment differs from driver 10 primarily in the outer diameter of cylindrical sleeve 150. Sleeve 150 has a distal shoulder 164 and a proximal shoulder 166, the diameter of each of which is the same and such that proximal shoulder 166 extends radially outwardly to define an annular compression surface 167 which extends radially outwardly as much as pin 152. This enables sleeve 150 to frictionally engage or retain a suture between shoulder 166 and pin 152 regardless of any rotation of sleeve 150 about axis 113. In this embodiment pin 152 serves to guide and retain the suture.

Figure 13:
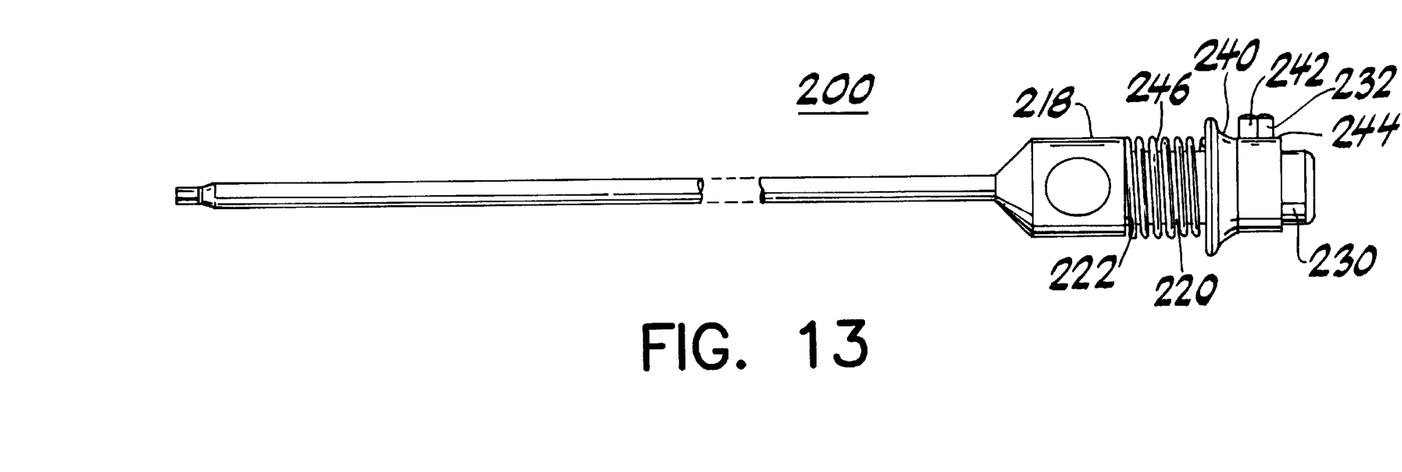
FIG. 13 is a side elevational view of another alternate embodiment of a suture anchor driver constructed in accordance with the principles of this invention.
Figure 14:
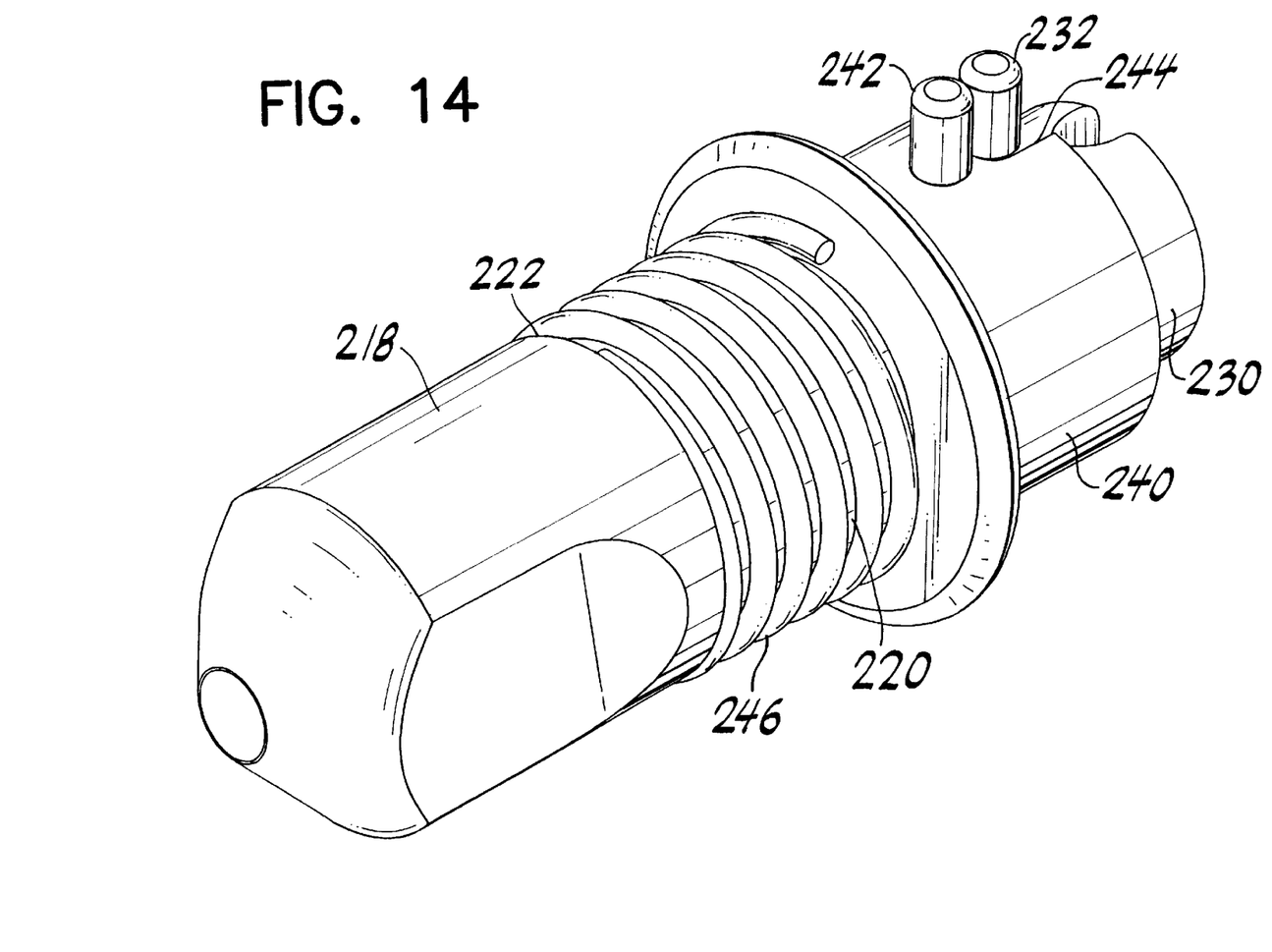
FIG. 14 is a front perspective view of the proximal portion of the embodiment of FIG. 13.

Another alternate embodiment of the invention is shown in FIGS. 13 and 14 as suture anchor driver 200 which differs from driver 10 only in the configuration of handle portion 218. Handle portion 218 has a recess 220 bounded by a single distal shoulder 222, the diameter of recess portion 220 being uniform from shoulder 222 to the proximal end 230 of the driver. A fixed retention post 232 is secured to the handle and a cylindrical sleeve 240 is provided with a post 242 extending from its circumferential outer surface adjacent a slot 244. The slot enables post 242 to be positioned contiguously with post 232. Sleeve 240 and post 242 are movable as a unit biased by spring 246 and it will be understood that suture is retained in this embodiment by a friction fit between posts 232 and 242. Post 232 may be threaded into the handle so that it may be easily removed to facilitate the disassembly and cleaning of this embodiment.

Figure 15:
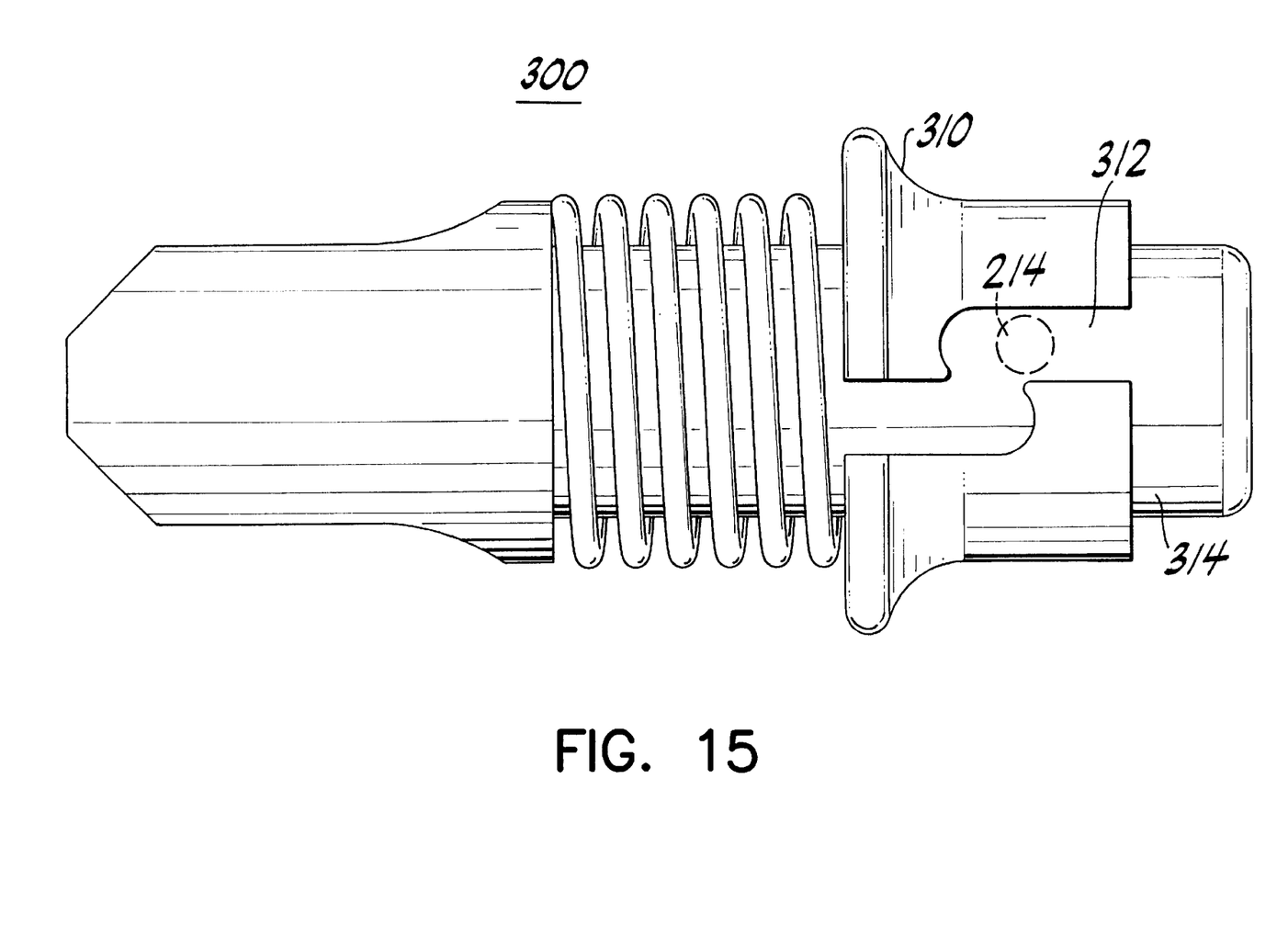
FIG. 15 is a plan view of another alternate embodiment of a portion of the embodiment of FIG. 14.

As shown in FIG. 15, an alternate embodiment 300 of handle 218 utilizes all of the features described above with respect to driver 200 except that cylindrical sleeve 240 is replaced by cylindrical sleeve 310 having an S-shaped channel 312 extending through the body of the sleeve. The embodiment may utilize posts similar to post 232 and 242 although they are omitted for clarity. The movable post (comparable to 242) would, for example, be on the diametrically opposite side of the sleeve from channel 312 and not seen in FIG. 15. Channel 312 enables sleeve 310 to be removed from body 314 of the handle portion by rotating the sleeve about the axis of the handle and placing channel 212 in alignment with the fixed post (comparable to 232). Manipulating the fixed post (represented by phantom circle 214) through the S-shaped channel 312 would enable sleeve 310 to be moved proximally past the fixed pin so the device could be disassembled for cleaning.

The embodiments disclosed herein may be made either reusable or disposable and either pre-loaded or not. In either event, the various components of the drivers may be made of biocompatible metals or plastics which, if designed for reuse, are sterilizable without the degradation suffered by prior art devices such as grommets and the like.

It will be understood by those skilled in the art that numerous improvements and modifications may be made to the preferred embodiment of the invention disclosed herein without departing from the spirit and scope thereof.

What is claimed is:

1. A driver for driving a suture anchor having suture attached thereto, the driver comprising:
   an elongated shaft having an axis, a proximal end and a distal end;
   an anchor receiving means at the distal end of said shaft for receiving a suture anchor to be driven;

means for enabling suture to pass from said distal end to said proximal end of said shaft; and suture retaining means at the proximal end of said shaft for retaining said suture, said retaining means comprising:

a fixed retention means immovably secured to said shaft for guiding said suture in a predetermined direction, said fixed retention means comprising a radially outwardly extending projection;

a movable compression means for frictionally engaging said suture, said compression means longitudinally movably attached to said shaft;

spring means for urging said compression means toward said fixed retention means to retain suture therebetween.

2. A driver according to claim 1 wherein said compression means is cylindrical and has an axis in alignment with said axis of said elongated shaft.

3. A driver according to claim 1 further comprising radially extending channel means at the proximal-most end of said shaft for communicating suture from said passage enabling means to said fixed retention means.

4. A driver according to claim 1 wherein said suture retaining means further comprises:

a first annular shoulder radially outwardly extending from said shaft and a second annular shoulder radially outwardly extending from said shaft, said second annular shoulder situated proximally relative to said first annular shoulder, and wherein said movable compression means comprises a cylindrical sleeve having a proximally facing surface adapted to slidably move between said first and second annular shoulders and wherein said spring means comprises a coil spring situated between said first and second shoulders to urge said cylindrical sleeve proximally.

5. A driver according to claim 4 wherein the outer diameter of said cylindrical sleeve is equal to the outer diameter of said second annular shoulder.

6. A driver according to claim 4 wherein said coil spring is axially aligned with the axis of said elongated shaft and the diameter of said elongated shaft is less than the diameter of said coil spring.

7. A driver for driving a suture anchor having suture attached thereto, the driver comprising:

an elongated shaft having an axis, a proximal end and a distal end;

an anchor receiving means at the distal end of said shaft for receiving a suture anchor to be driven;

means for enabling suture to pass from said distal end to said proximal end of said shaft;

suture retaining means at the proximal end of said shaft for retaining said suture, said retaining means comprising:

a fixed post means immovably secured to said shaft for guiding said suture in a predetermined direction;

a movable compression means for frictionally engaging said suture, said compression means movably attached to said shaft;

spring means for urging said compression means against said fixed post means to retain suture therebetween.

8. A driver according to claim 7 wherein said movable compression means comprises a cylinder having a circumferential surface and an axial throughbore adapted to slidably engage said shaft.

9. A driver according to claim 8 wherein said fixed post extends a first predetermined radial distance from said axis and wherein said cylinder further comprises an annular compression surface extending outwardly a first predetermined radial distance.

10. A driver according to claim 8 wherein said cylinder further comprises a longitudinally extending serpentine channel, having a width adapted to pass said fixed post means therethrough, for enabling said cylinder to be moved proximally past said fixed post means.

11. A method for securing a suture anchor, with suture attached thereto, to a driver having an external surface, a proximal end, a distal end and an anchor engaging means at said distal end for engaging said anchor, said method comprising the steps of:

passing said suture from said distal end to said proximal end;

seating said anchor in said anchor engaging means;

providing at said proximal end a spring actuated suture retaining means for retaining suture, said retaining means comprising a fixed radially extending retention means immovably secured to said driver for guiding said suture in a predetermined direction, a longitudinally movable compression means movably attached to said driver and spring means for urging said compression means toward said fixed radially extending retention means to retain suture therebetween;

retracting and holding said movable compression means to form a predetermined space between it and said fixed radially extending retention means;

passing said suture from said proximal end into said predetermined space; and releasing said movable compression means to enable it to move longitudinally to thereby secure said suture between said movable compression means and said fixed retention means.

12. A method according to claim 11 wherein said fixed retention means is a radially outwardly extending projection subtending a predetermined arcuate distance along said external surface of said driver and wherein said method further comprises the step of guiding said suture contiguously past said projection and into said predetermined space.

13. A method for securing a suture anchor, with suture attached thereto, to a driver having a proximal end, a distal end and an anchor engaging means at said distal end for engaging said anchor, said method comprising the steps of:

passing said suture from said distal end to said proximal end;

seating said anchor in said anchor engaging means;

providing at said proximal end a spring actuated suture retaining means for retaining suture, said retaining means comprising a fixed retention means immovably secured to said driver for guiding said suture in a predetermined direction, said fixed retention means comprising a radially outwardly extending projection, a movable compression means movably attached to said driver and spring means for urging said compression means toward said fixed retention means to retain suture therebetween;

retracting and holding said movable compression means to form a predetermined space between it and said fixed retention means;

guiding said suture from said proximal end contiguously past said projection and into said predetermined space; and releasing said movable compression means to enable it to move longitudinally to thereby secure said suture between said movable compression means and said fixed retention means.

* * * * *